(12) United States Patent
Khachigian

(10) Patent No.: US 6,200,960 B1
(45) Date of Patent: Mar. 13, 2001

(54) INHIBITION OF PROLIFERATION OF CELLS

(75) Inventor: Levon Michael Khachigian, Ryde (AU)

(73) Assignee: Unisearch Limited (AU)

( * ) Notice: Subject to any disclaimer, the term of this patent is extended or adjusted under 35 U.S.C. 154(b) by 0 days.

(21) Appl. No.: 09/142,779

(22) PCT Filed: Mar. 7, 1997

(86) PCT No.: PCT/AU97/00140

§ 371 Date: Apr. 13, 1999

§ 102(e) Date: Apr. 13, 1999

(87) PCT Pub. No.: WO97/32979

PCT Pub. Date: Dec. 9, 1997

(30) Foreign Application Priority Data

Mar. 7, 1996 (AU) .................................................. PN8554

(51) Int. Cl.$^7$ ............................. C07H 21/04; C12Q 1/68; C12N 15/8586; A61K 31/70; A01N 43/04

(52) U.S. Cl. ............................... 514/44; 435/6; 435/91.1; 435/91.31; 435/325; 435/375; 536/23.1; 536/24.3; 536/24.5; 514/44

(58) Field of Search .................... 435/91.1, 6, 91.31, 435/440, 375, 325; 536/23.1, 23.2, 24.5, 24.3; 514/44

(56) References Cited

U.S. PATENT DOCUMENTS 5,206,152 4/1993 Sukhatme .............................. 435/69.1

OTHER PUBLICATIONS

Muthukkumar et al. Role of EGR–1 in thapsigargin–inducible Apoptosis in the Melanoma Cell Line A375–C6. Molecular and Cellular Biology, vol. 15, No. 11, pp. 626–6272, Nov. 1995.*

Adams et al., Initial assessment of human gene diversity and expression patterns based upon 83 million nucleotides of cDNA sequence, Nature, vol. 377, Suppl. 6547, 3–174 (1995).*

Hu, R. et al., "Astrocyte Growth is Regulated by Neuropeptides Through Tis 8 and Basic Fibroblast Growth Factor," *The Journal of Clinical Investigation*, (Apr. 1994), vol. 93, pp. 1820–1827.

Ackerman, S. L. et al. (Sep. 1991). "Functional significance of an overlapping consensus binding motif for Sp1 and Zif268 in the murine adenosine deaminase gene promoter," *Proc. Natl. Acad. Sci. U. S. A.* 88:7523–7527.

Barret, T B. and E. P. Benditt. (Feb. 1987). "Sis (platelet–derived growth factor B chain) gene transcript levels are elevated in human atherosclerotic lesions compared to normal artery," *Proc. Natl. Acad. Sci. U. S. A.* 84:1099–1103.

Barrett, T. B. and E. P.Benditt. (Apr. 1988). "Platelet–derived growth factor gene expression in human atherosclerotic plaques and normal artery wall," *Proc. Natl. Acad. Sci. U. S. A.* 85:2810–2814.

Bennett, M. R. and S. M. Schwartz. (Oct. 1, 1995). "Antisense therapy for angioplasty restenosis," *Circulation.* 92(7):1981–1993.

Burgess, T. L. et al. (Apr. 1995). "The antiproliferative activity of c–myb and c–myc antisense oligonucleotides in smooth muscle cells is caused by a nonantisense mechanism," *Proc. Natl. Acad. Sci. U. S. A.* 92:4051–4055.

Cazenave, C. et al. (1989) "Comparative inhibition of rabbit globin mRNA translation by modified antisense oligodeoxynucleotides," *Nucl. Acids Res.* 17(11):4255–4273.

Crooke, R. M. (1991). "In vitro toxicology and pharmacokinetics of antisense oligonucleotides," *Anti–Cancer Drug Design.* 6:609–646.

Dirks, R. P. H. (1995). "In vivo footprinting and functional analysis of the human c–sis/PDGF B gene promoter provides evidence for two binding sites for transcriptional activators," *Nucl. Acids Res.* 23(7):1119–1126.

Ferns, G. A. A. et al. (1990). "Relative platelet–derived growth factor receptor subunit expression determines cell migration to different dimeric forms of PDGF," *Growth Factors.* 3:315–324.

Ferns, G. A. A. et al. (Sep. 6, 1991). "Inhibition of neointimal smooth muscle accumulation after angioplasty by an antibody to PDGF," *Science.* 253:1129–1132.

Gashler, A. and V. P. Sukhatme. (1995). "Early growth response protein1 (Egr–1): Prototype of a Zinc–finger family of Transcription factors," *Prog. Nucl. Acid Res. and Molec. Biol.* 50:191–224.

Gimbrone, Jr., M. A. (1995). "Vascular endothelium: An integrator of pathophysiologic stimuli in artherosclerosis," *Am. J. Cardiol.* 75:67B–70B.

Hallahan, D. E. et al. (Dec. 22, 1995). "C–jun and Egr–1 participate in DNA synthesis and cell survival in response to ionization radiation exposure," *J. Biol. Chem.* 270(51):30303–30309.

Jawien, A. et al. (Feb. 1992). "Platelet–derived growth factor promotes smooth muscle migration and intimal thickening in a rat model of balloon angioplasty," *J. Clin. Invest.* 89:507–511.

(List continued on next page.)

*Primary Examiner*—Robert A. Schwartzman
*Assistant Examiner*—Janet Epps
(74) *Attorney, Agent, or Firm*—Morrison & Foerster LLP

(57) ABSTRACT

The present invention provides a method of inhibiting the proliferation of cells. The method comprises inhibiting induction or decreasing expression of Egr-1 or decreasing the nuclear accumulation or activity of the Egr-1 gene product. The present invention also provides a method of reducing the incidence of restenosis in a subject. The method comprises administering to the subject an agent which inhibits induction or decreases expression of Egr-1 or decreases the nuclear accumulation or activity of the Egr-1 gene product.

8 Claims, 2 Drawing Sheets

OTHER PUBLICATIONS

Juliano, R. L. and S. Akhtar. (1992). "Liposomes as a drug delivery system for antisense oligonucleotides," *Antisense Res. and Devel.* 2:165–176.

Khachigian, L. M. et al. (Sep. 9, 1994). "Novel cis–acting elements in the human platelet–derived growth factor B–chain core promoter that mediate gene expression in cultured vascular endothelial cells," *J. Biol. Chem.* 269(36):22647–22656.

Khachigian, L. M. et al. (Nov. 1995). "Interplay of Sp1 and Egr–1 in the proximal platelet–derived growth factor A–chain promoter n cultured vascular endothelial cells," *J. Biol. Chem.* 270(46):27679–27686.

Khachigian, L. M. et al. (Mar. 8, 1996). "Egr–1—Induced endothelial gene expression: A common theme in vascular injury," *Science.* 271:1427–1431.

Kozak, M. (1986). "Influences of mRNA secondary structure on initiation by eukaryotic ribosomes," *Proc. Natl. Acad. Sci. U. S. A.* 83:2850–2854.

Libby, P. et al. (Jun. 9, 1988). "Production of platelet–derived growth factor–like mitogen by smooth–muscle cells from human atheroma," *New Eng. J. Med.* 318(23):1493–1498.

Lidner V. and M. A. Reidy. (Jun. 1995). "Platelet–derived growth factor ligand and receptor expression by large vessel endothelium in vivo," *Am. J. Pathol.* 146(6):1488–1497.

Loke, S. L. et al. (May 1989). "Characterization of oligonucleotide transport into living cells," *Proc. Natl. Acad. Sci. U. S. A.* 86:3474–3478.

Majesky, M. W. et al. (Nov. 1990). "PDGF ligand and receptor gene expression during repair of arterial injury," *J. Cell Biol.* 111:2149–2158.

Marcus–Sekura, C. J. (1987). "Comparative inhibition of chloramphenicol acetyltransferase gene expression by anti-sense oligonucleotide analogues having alkyl phospohtri-ester, methylphosphonate and phosphorothioate linkages," *Nucl. Acids Res.* 15(14):5749–5763.

Mattsson, E. and A. W. Clowes. (1995). "Current concepts in restenosis following balloon angioplasty," *TCM.* 5(5):200–204.

Murry, C. E. et al. (Mar. 15, 1996). "Platelet–derived growth factor–A mRNA expression in fetal, normal adult, and atherosclerotic human aortas," *Circulation.* 93(6):1095–1106.

Muthukrishan L. et al. (1991). "Basic fibroblast growth factor is efficiently released from a cytolsolic storage site through plasma membrane disruptions of endothelial cells," *J. Cell. Physiol.* 148:1–16.

Nabel, E. G. et al. (Apr. 1993). "Recombinant platelet–derived growth factor B gene expression in porcine arteries induces intimal hyperplasia in vivo," *J. Clin. Invest.* 91:1822–1829.

Nicod, P. and R. Scherrer. (May 1993). "Explosive growth of coronary angioplasty," *Circulation.* 87(5):1749–1751.

Rekhter, M. D. and D. Gordon. (Sep. 1994). "Does platelet–derived growth factor–A chain stimulate proliferation of arterial mesenchymal cells in human atherosclerotic plaques?," *Circulation. Res.* 75(3):410–417.

Ross, R. et al. (May 25, 1990). "Localization of PDGF–B protein in macrophages in all phases of atherogenesis," *Science.* 248:1009–1012.

Spiller, D. G. and D. M. Tidd. (1992). "The uptake kinetics of chimeric oligodeoxynucleotide analogues in human leu-kaemia MOLT–4 cells," *Anti–Cancer–Drug Design.* 7:115–129.

Stein, C. A. et al. (1993). "Dynamics of the internalization of phosphodiester oligodeoxynucleotides in HL60 cells," *Biochem.* 32:4855–4861.

Sukhatme, V. P. et al. (Apr. 8, 1988). "A Zinc finger–encoding gene coregulated with c–fos during growth and differentiation, and after cellular depolarization," *Cell.* 53:37–43.

Tsai–Morris, Chon–Hwa et al. (1988). "5' Flanking sequence and genomic structure of Egr–1, a murine mitogen inducible zinc finger encoding gene," *Nucl. Acids Res.* 16(18):8835–8846.

Villa, A. E. et al. (Apr. 1995). "Effects of antisense c–myb oligonucleotides on vascular smooth muscle cell proliferation and response to vessel wall injury," *Circ. Res.* 76(4):505–513.

Wagner, R. W. and K. Nishikura. (Feb. 1988). "Cell cycle expression of RNA duplex unwindase activity in mammalian cells," 8(2):770–777, Mol. Cell. Biol.

Wilcox, J. N. et al. (Sep. 1988). "Platelet–derived growth factor mRNA detection in human atherosclerotic plaques by in situ hybridization," *J. Clin. Invest.* 82:1134–1143.

Reissen et al. (1994). "Prospects for Site–Specific Delivery of Pharmacologic and Molecular Therapies," *J. Am Coll Cardiol* 23(5):1234–44.

Wilensky et al. (1993). "Methods and Devices for Local Drug Delivery in Coronary and Peripheral Arteries," *Trends Cariovasc Med* 3(5):163–170.

* cited by examiner

INHIBITION OF PROLIFERATION OF CELLS

FIELD OF THE INVENTION

The present invention relates to a method of inhibiting the activation of a gene which has in turn been shown to lead to the induction of a number of other genes that have been strongly implicated in the development of vascular disease such as atherosclerosis and restenosis. In addition, the present invention relates to oligonucleotides which can be used in this method. The invention seeks to inhibit the proliferation of cells, migration of cells to sites of injury and remodelling of vascular wall, associated with the pathogenesis of atherosclerosis or restenosis, such as smooth muscle cells or endothelial cells.

BACKGROUND OF THE INVENTION

Atherosclerosis is thought to originate from a subtle process of endothelial injury. Vascular endothelium constitutes a non-thrombogenic surface of normally quiescent cells that line blood vessels and regulate molecular and cellular movement across the vessel well. In response to denuding injury, endothelial cells at the wound edge spread and migrate into the vacant area, undergo proliferation and secrete factors that stimulate endothelial and smooth muscle cell growth. These responses provide an important homeostatic mechanism for maintaining normal vascular function. Growth factors such as platelet-derived growth factor (PDGF, which comprises an A chain and/or a B chain) and basic fibroblast growth factor (bFGF) have been implicated to play key roles in the regenerative events following vascular injury. The induction of PDGF gene expression in vascular endothelium may have profound chemotactic and mitogenic effects on the underlying smooth muscle cells and contribute to the structural remodelling that typically occurs in experimental arterial repair, restenosis and in the pathogenesis of atherosclerotic vascular disease (1). Smooth muscle cells are found in both fatty streaks and fibrous atherosclerotic plaques. Their proliferation and ability to form enormous amounts of connective tissue matrix and accumulate lipid are key contributing factors in the development of the atherosclerotic lesion.

Despite a wealth of descriptive studies which correlate the formation of vascular occlusive lesions with the inappropriate expression of these and other growth regulatory molecules (2), a direct link between a transcription factor and the induced expression of a pathophysiologically relevant gene has not yet been demonstrated in the context of arterial injury.

The treatment of occluded coronary arteries currently involves the use of percutaneous transluminal coronary angioplasty (PCTA) or more recently PCTA in conjunction with the placement of a device known as a stent. PCTA is a balloon device that is delivered to the affected site via a catheter and following expansion of the balloon results in physical removal of the blocking plaque or thrombus and enlargement of the local vessel area.

The application of the stent, a fenestrated metallic sleeve, adds additional support to the re-opened vessel and amongst other benefits, prevents the frequency of elastic recoil of the vessel wall. In some of the cases of intervention the benefit of the treatment is short lived and the vessel undergoes reclosure or restenosis. Restenosis is a multi-phased clinical event and can involve elastic recoil in the first instance followed by extensive vascular remodelling and luminal shrinkage. The final stages of the restenotic process involve recruitment and proliferation of smooth muscle cells to create a neo-intimal mass between the elastic lamina and the endothelium. The incidence of restenosis has gradually reduced with the advancement of healthcare methods but is still a significant problem (Kimura et al. (1996) New England Journal of Medicine 335:561–566, Bittl, (1996) New England Journal of Medicine 334:1290–1302).

There is considerable activity focussed on the development of pharmaceuticals to be used as adjuncts to the interventional methods in an attempt to reduce the incidence of restenosis. Some of the classes of drugs under development include:

(a) Anticoagulants—agents such as hirudin and bivalirudin target the formation of thrombin rich clots.

(b) Antiplatelet drugs—suppression of platelet activation can reduce the formation of platelet aggregates and clotting. One approach involves the use of a monoclonal antibody dubbed Abciximab that is specific for the platelet fibrinogen receptor glycoprotein IIb/IIIa.

(c) Antiproliferatives—Trapidil is an antagonist of the PDGF receptor. PDGF is an established stimulator of smooth muscle cell recruitment and proliferation and it is proposed that inhibition of PDGF activity will inhibit this activity.

(d) Antioxidants—compounds such as Probucal are currently under investigation as agents to remove oxidative stress from vessel walls and thus limit the smooth muscle cell proliferation associated with such stress.

(e) Nucleic acid based therapies—antisense and ribozymes directed against specific targets e.g. WO 96/25491, WO 96/20279 and WO 96/11266

SUMMARY OF THE INVENTION

It has been found that Egr-1 is rapidly activated following arterial injury. Induced Egr-1 binds to, and stimulates expression from, the control regions of several genes whose products cause cell proliferation, cell recruitment and vascular wall remodelling of vascular cells.

Accordingly, in a first aspect, the present invention consists in a method of inhibiting proliferation of cells comprising inhibiting induction or decreasing expression of Egr-1 or decreasing the nuclear accumulation or activity of the Egr-1 gene product.

In a preferred embodiment the cells are vascular cells, particularly smooth muscle or endothelial cells. The cells may, however, be cells involved in neoplasia.

As will be recognised by those skilled in this field there are a number means by which the method of the present invention may be achieved. These include the following:

(a) Targeting the Egr-1 gene directly using triple helix (triplex) methods in which a ssDNA molecule can bind to the dsDNA and prevent transcription.

(b) Inhibiting transcription of the Egr-1 gene using nucleic acid transcriptional decoys. Linear sequences can be designed that form a partial intramolecular duplex which encodes a binding site for a defined transcriptional factor. Evidence suggests that Egr-1 transcription is dependent upon the binding of Sp1. AP1 or serum response factors to the promoter region. It could be envisaged that inhibition of this binding of one or more of these transcription factors would inhibit transcription of the Egr-1 gene.

(c) Inhibition of translation of the Egr-1 mRNA using synthetic antisense DNA molecules that do not act as a substrate for RNase H and act by sterically blocking gene expression.

(d) Inhibition of translation of the Egr-1 mRNA by destabilising the mRNA using synthetic antisense DNA molecules that act by directing the RNase H-mediated degradation of the Egr-1 mRNA present in the heteroduplex formed between the antisense DNA and mRNA.
(e) Inhibition of translation of the Egr-1 mRNA by destabilisation of the Egr-1 mRNA by cleavage of the mRNA by sequence-specific hammerhead ribozymes and derivatives of the hammerhead ribozyme such as the Minizymes or Mini-ribozymes or where the ribozyme is derived from:
  (i) the hairpin ribozyme,
  (ii) the Tetrahymena Group I intron,
  (iii) the Hepatitis Delta Viroid ribozyme or
  (iv) the Neurospera ribozyme.
The composition of the ribozyme could be:
  (i) made entirely of RNA,
  (ii) made of RNA and DNA bases,
or
  (iii) made of RNA or DNA and modified bases, sugars and backbones
The ribozyme could also be either:
  (i) entirely synthetic or
  (ii) contained within a transcript from a gene delivered within a virus-derived vector, expression plasmid, a synthetic gene, homologously or heterologously integrated into the patients genome or delivered into cells ex vivo, prior to reintroduction of the cells of the patient, using one of the above methods.
(f) Inhibition of translation of the Egr-1 mRNA by cleavage of the mRNA by sequence-specific catalytic molecules composed of DNA. For example molecules described previously by Breaker and Joyce (Breaker and Joyce (1995) Chemistry and Biology 2:655–660) could be developed to cleave Egr-1 mRNA.
(g) Inhibition of Egr-1 activity as a transcription factor using transcriptional decoy methods. A method according to that described in (b) above could be used that would interfere with Egr-1 activity and consequent induction of Egr-1-dependent genes.
(h) Inhibition of the activity of the Egr-1 gene protein by antisense oligonucleotides that have the potential to hybridise specifically to the Egr-1 mRNA and contain four consecutive G residues. These G residues are required for the effect of the oligo in preventing restenosis or atherosclerosis. See WO 96/11266 "Method for inhibiting smooth muscle cell proliferation and oligonucleotides for use therein".
(i) Inhibition of the ability of the Egr-1 gene to bind to its target DNA by drugs that have preference for GC rich sequences. Such drugs include nogalamycin, hedamycin and chromomycin $A_3$ (Chiang et al J. Biol. Chem. 1996; 271:23999).

In a second aspect the present invention consists in an oligonucleotide for use in decreasing biosynthesis of Egr-1, the oligonucleotide having the sequence ACA CTT TTG TCT GCT (SEQ ID NO:1).

As will be readily recognised by those skilled in the art the process of restenosis involves proliferation of smooth muscle cells. Endothelial and smooth muscle cells activated by injury inducibly express genes whose products are mitogenic and chemotactic to these cells. Accordingly it is believed that the method of the present invention may have particular application in the inhibition or reduction of occurrence of this condition.

Accordingly, in a third aspect the present invention consists in a method of reducing the incidence of restenosis in a subject the method comprising administering to the subject an agent which inhibits induction or decreases expression of Egr-1 or decreases the nuclear accumulation or activity of the Egr-1 gene product.

As will be understood by those skilled in the art there are a number of methods by which the agents which inhibit induction or decrease expression of Egr-1 or decrease the nuclear accumulation or activity of the Egr-1 gene product may be administered. A useful review of a number of these delivery routes is provided by Reissen et al (J Am Coll Cardiol 1994;223:1234–44) and Wilensky et al (Trends Cardiovasc Med 1993:3:163–170), the disclosures of which are incorporated herein by reference.

In particular, delivery of the nucleic acid agents described may be achieved by one or more of the following methods:
  (a) Liposomes and liposome-protein conjugates and mixtures.
  (b) Using catheters to deliver intra-luminal formulations of the nucleic acid as a solution or in a complex with a liposome.
  (c) Catheter delivery to adventitial tissue as a solution or in a complex with a liposome.
  (d) Within a polymer such as Pluronic gels or within ethylene vinyl acetate copolymer (EVAc). The polymer will be delivered intra-luminally.
  (e) Within a vital-liposome complex, such as Sendal virus.
  (f) The nucleic acid may be delivered by a double angioplasty balloon device fixed to catheter.
  (g) The nucleic acid could be delivered on a specially prepared stent of the Schatz-Palmaz or derivative type. The stent could be coated with a polymer or agent impregnated with nucleic acid that allows controlled release of the molecules at the vessel wall.

As used herein the term DNA refers to primarily to deoxyribonucleotides it will, however, be readily apparent to those skilled in the art that derivatives of DNA may be used. It is intended that such derivatives are included in the scope of the present invention. The envisaged modifications are well known to those skilled in the art and include:
  (a) phosphodiester backbone modification by replacement of a non-bridging oxygen atom with sulphur or a methyl group such as in phosphorothioates or methylphosphonates or replacement of phosphodiester backbone with a peptide linked backbone such as in PNAs.
  (b) replacement of the 2' hydrogen within the deoxyribose group with a amine, methyl or other alkanes or alkenes or other functional group.
  (c) modification of the termini of the oligonucleotide by the addition of an inverted base at the 3' end via 3'—3' linkages.
  (d) modification of 5' and 3' by conjugation of other functional groups selected from lipids and steroids such as cholesterol.
  (e) phosphodiester backbone modifications in which the phospho-sugar backbone is replaced by a morphilino phophorodiamidate backbone.

It will also be understood that similar modifications may be applied to the RNA oligonucleotides except in (b) the 2' group that would be replaced would by hydroxyl.

DETAILED DESCRIPTION OF THE INVENTION

In order that the nature of the present invention may be more clearly understood the preferred forms of the present invention will now be described in greater detail.

FIGURE LEGENDS

Figure 1:
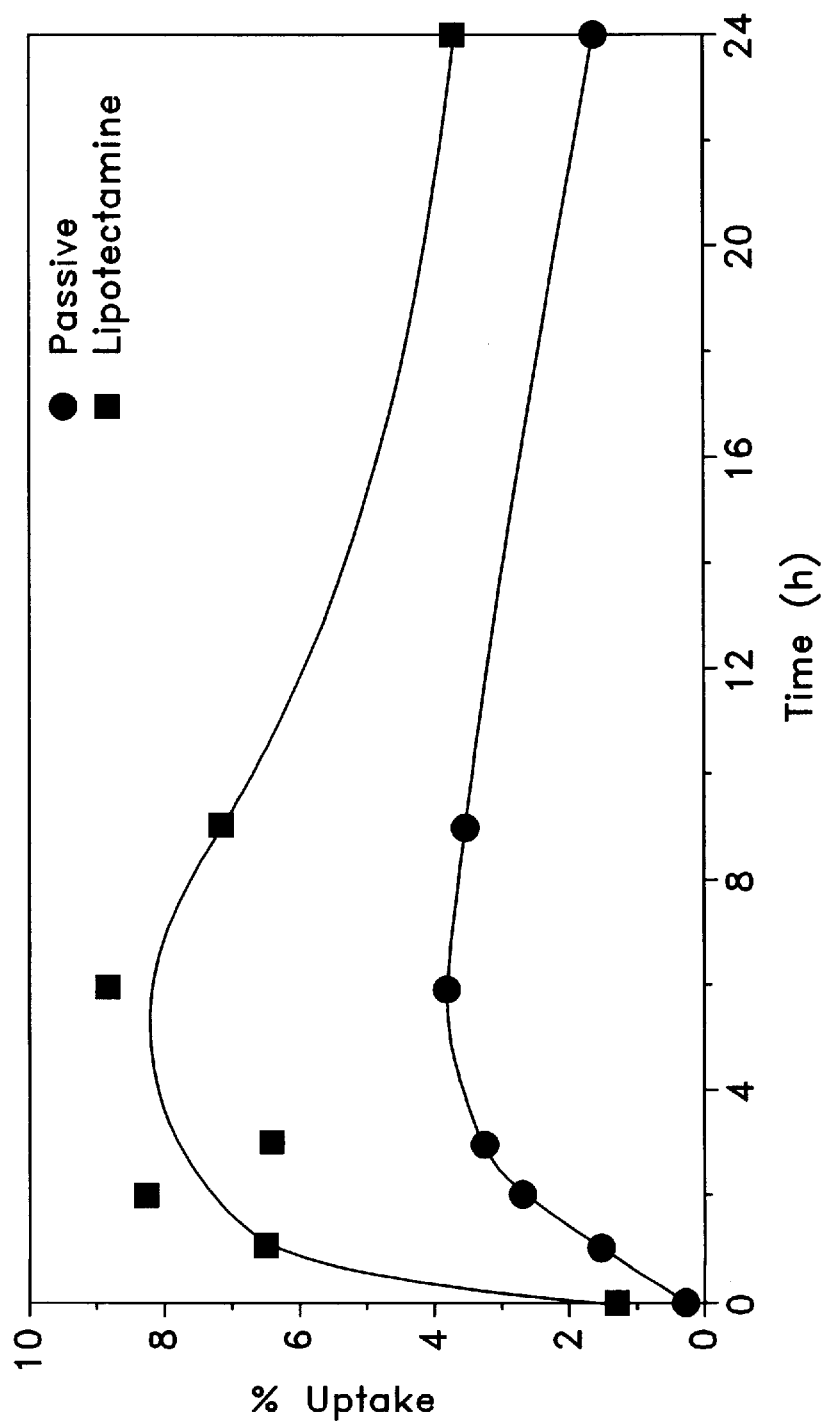
FIG. 1 shows uptake of radiolabeled antisense E11 by smooth muscle cells (● passive; ■ "Lipofectamine").

In a survey of immediate-early genes that could be induced by acute vascular injury in the rat aorta, the expression of the early-growth-response gene product Egr-1 (krox-24; NGF-IA, zif268, T1S8), a serum-inducible zinc-finger nuclear phosphoprotein and member of a family of related transcription factors (3) was examined. In this examination aortic endothelium of male Sprague-Dawley rats (400 g) was partially denuded using an uninflated 2F balloon catheter. Deendothelialized regions were identified by intravenous injection of Evans blue (0.3 ml of 5% solution in PBS) 10 min prior to sacrifice. Animals were perfusion-fixed with phosphate-buffered 4% paraformaldehyde. Vessel segments were treated with 1 μg/ml proteinase at 37° C., prehybridized for 2 h at 55° C. in 0.3M NaCl, 20 mM Tris, pH7.5, 5 mM EDTA, 1×Denhardt's, 10% DTT and 50% formamide, and incubated with the appropriate $^{35}$S-UTP-labeled riboprobe for 16 h. After washing, the slides were coated with autoradiographic emulsion and exposed for 3 wk. The images were photographed and digitized. The hybridization signal of the radiolabeled probe appears as white grains. All specimens observed under dark field illumination after nuclear counterstain with hematoxylin. Immunostaining for factor-VIII-related antigen confirmed that injury was limited to endothelium.

In situ hybridization techniques which visualize the endothelium of the vessel wall en face revealed that Egr-1 expression was dramatically induced exclusively at the endothelial wound edge within 30 min of partial denudation. Egr-1 expression was undetectable in endothelium from unmanipulated arteries. Induced Egr-1 mRNA was apparent after 2 h, and the time-dependent decrease in the specific hybridization signal demonstrates the transient induction of endothelial Egr-1 expression by injury. In contrast, the sense Egr-1 riboprobe failed to hybridize with mRNA from normal or injured tissue. PDGF-B-chain transcript levels were also low in unmanipulated vessels, consistent with previous findings using other techniques (4). Partial denudation did not induce PDGF-b gene expression at the endothelial wound edge until 4 h after injury and continued for several weeks during endothelial regeneration (5). The colocalization of the spatial patterns of Egr-1 and PDGF-B gene expression, and the temporal association between these two genes in injured arterial endothelium, led to a determination of whether Egr-1 could inducibly regulate the expression of PDGF-B.

In response to mechanical injury in vitro, confluent endothelial cells initiate movement into the open "wounded" area by actively responding to locally-derived signals or autocoids from injured cells. An in vitro model of vascular injury (6) was used to address the possible link between Egr-1 and injury-induced PDGF-B gene expression. Nuclear run-off analysis revealed that Egr-1 gene transcription was induced in cultured bovine aortic endothelial cells (BAEC) within 1 h of injury. 5' deletion analysis of the PDGF-B promoter in endothelial cells previously defined a region necessary for core promoter activity (d77) which contained a binding site for the ubiquitous transcription factor, Sp1 (7). Recent in vivo footprint analysis of the promoter demonstrates that the Sp1 element is indeed occupied in intact cells (8). In vitro DNase I footprinting revealed that recombinant Egr-1 protected a region overlapping this site from partial DNase I digestion. When nuclear extracts from endothelial cells 1 h after injury were incubated with a $^{32}$P-labelled oligonucleotide spanning this region ($^{32}$P-Oligo B, 5'-GCTGTCTCCACCCACCTCTCGCACTCT-3' SEQ ID NO:2), a distinct nucleoprotein complex formed. The injury-induced complex was eliminated by antibodies to Egr-1. Nuclear Sp1 also bound to the PDGF-B promoter fragment; however, its levels are unaltered by injury. Thus, injury-induced endothelial Egr-1 expression precedes the induction of PDGF-B, and Egr-1 binds to a distinct region in the PDGF-B promoter also bound by Sp1.

The functional importance of this interaction for PDGF-B promoter-dependent gene expression was next determined. Northern blot and transient transfection analysis using PDGF-B promoter-reporter constructs previously revealed that this gene is basally expressed in vascular endothelial cells (7). Chloramphenicol acetyltransferase (CAT) expression driven by the PDGF-B promoter (d77-CAT) was induced by injury within 36 h. Reporter activity also increased in cells exposed to phorbol 12-myristate 13-acetate (PMA) or by cytomegalovirus-mediated overexpression of Egr-1. When a mutation that abolished the ability of Egr-1 to bind to the PDGF-B promoter was introduced into the d77-CAT construct, basal expression driven by the promoter was attenuated, and expression inducible by injury was abolished. The mutant construct also failed to mediate increased reporter activity when Egr-1 was overexpressed, or when the cells were exposed to PMA. The Egr-1 binding site in the proximal PDGF-B promoter is thus required for inducible promoter-dependent expression in vascular endothelial cells.

The interaction of Egr-1 and Sp1 with overlapping binding elements in the proximal PDGF-B promoter suggests that Sp1, resident on the promoter in unstimulated cells, may be displaced by increasing levels of Egr-1. Running gel shifts (9) indicate that recombinant Egr-1 bound to the PDGF-B promoter in a stable and reversible manner. The relative efficiency with which Egr-1 was displaced from $^{32}$P-Oligo B by its unlabelled counterpart indicates that Egr-1 interacts with the PDGF-B promoter with a faster off-rate than its comparable site in the proximal PDGF-A promoter (9). Sp1 was displaced from the promoter by Egr-1 in a dose-dependent manner. Decreasing levels of Egr-1 in the presence of a fixed concentration of SP1 allowed reoccupation of the promoter by Sp1. The absence of a higher order complex when both factors are present indicates that Egr-1 and Sp1 do not bind the promoter simultaneously. These findings with recombinant proteins indicate that an interplay involving Egr-1 and Sp1 can occur on the PDGF-B promoter.

The localized induction of Egr-1 at the endothelial wound edge precluded a direct determination of whether a displacement mechanism was involved in the induction of PDGF-B gene expression by injury. PMA is a model agonist of Egr-1 expression in vascular endothelial cells (9). The dramatic induction of Egr-1 mRNA and protein that precedes the increase in PDGF-B levels in endothelial cells exposed to PMA is like the temporal pattern with which these genes are expressed at the endothelial wound edge following arterial balloon injury. Transcript and protein levels of Sp1 are also not affected by PMA. Nuclear proteins from PMA-treated endothelial cells bound to the PDGF-B promoter with a pattern similar to that observed using injury-induced extracts. Immunobinding studies determined that nucleoprotein complexes contained either Sp1 or Egr-1. The profound induction in Egr-1 levels by PMA demonstrates the ability of this transcription factor to displace Sp1 from the PDGF-B promoter in the context of nuclear extracts. Accordingly, the PMA-inducible endothelial expression of the PDGF-B gene, like PDGF-A (9), involves an interplay between Egr-1 and Sp1 at overlapping binding sites in the proximal promoter. This contrasts with a previous report suggesting that Egr-1 may serve as a negative regulator of gene transcription by blocking the binding of Sp1 to its own recognition sequence (10). These findings suggest that the localized induction of PDGF-B expression at the endothelial wound edge may also involve displacement of promoter-bound Sp1 by elevated levels of nuclear Egr-1. Egr-1 may be involved in interactions with other transcriptional activators and the basal complex to mediate increased gene expression in response to injury.

Egr-1 also appears to play a key role in injury-inducible PDGF expression in smooth muscle cells. In the rat arterial injury model in-situ hybridization with en face preparations indicate that Egr-1 expression is induced in smooth muscle cells concurrent with the expression of PDGF-A at the same location.

Antisense Approach

The antisense approach is based on the ability of an oligonucleotide (synthetic DNA) to recognize its complementary sequence within the cell, in the form of messenger RNA; the bound complex is then able to sterically interfere with ribosome binding and translation into protein (11). Alternatively, the bound complex triggers cleavage of the mRNA by the nuclease RNase H, which is widely present in mammalian cells and specifically recognizes DNA-RNA duplexes (12). Thus, the overall effect of a given antisense oligonucleotide may be to reduce specific mRNA and protein levels if mediated by RNase H, or a reduction in specific protein levels in the case of steric interference (13).

Advantages offered by the use of antisense oligonucleotides over conventional inhibitors are specificity and synthesis. This is based on the uniqueness of the target mRNA and the general availability of oligonucleotide synthesizers. A drawback in this approach is the propensity of these oligonucleotides to be degraded or inactivated by nucleolytic phosphodiesterases. However, chemical modification of the phosphodiester linkages between individual nucleotides has been found to increase nuclease resistance by up to ten-fold and increase potency as a consequence (14,15).

As explained above Egr-1 is an immediate-early gene (16,17) expressed at low or undetectable levels in arterial endothelial cells (18) or smooth muscle cells. It is dramatically induced by a number of (patho)physiologically-relevant agonists and conditions such as fluid shear stress, mechanical injury (18), heparin-binding growth factor-1, as well as the protein kinase C-inducer, phorbol 12-myristate 13-acetate (9). Egr-1 mRNA is transcribed and processed in the nucleus; it then enters the cytoplasm where it is translated to protein. Since Egr-1 protein contains a nuclear targeting sequence, it reenters the nucleus and interacts with its nucleotide recognition sequence in the promoters of responsive genes. Two genes which are induced by Egr-1 are those encoding the platelet-derived growth factor A-chain (9) and B-chain (18). This growth factor is a potent mitogen and chemoattractant for smooth muscle cells (19) and produced by cells involved in the atherosclerotic or restenotic lesion. Accordingly, the PDGF ligand/receptor signalling system has been implicated in the pathogenesis of atherosclerosis.

Elevated levels of PDGF-A transcripts have been observed in human carotid plaques (20). The coexpression of PDGF-A with smooth muscle α-actin implicated SMCs in the plaque as a source of PDGF-A (20). Murry and colleagues (21) also found PDGF-A mRNA in human atherosclerotic plaques using competitive RT-PCR. Rekhter and Gordon (22) used a triple immunolabeling approach to localize PDGF-A protein to smooth muscle-like cells and some endothelial cells within human carotid plaques. Libby and colleagues showed that SMCs cultured from human atherosclerotic plaques could express PDGF-A transcripts and secrete PDGF-like binding and mitogenic activity (23). Barrett and Benditt used Northern blot and dot blot analysis to show that levels of PDGF-B-chain mRNA were approximately five-fold greater in carotid plaques than normal aorta and carotid arteries (24). In situ hybridization later corroborated these findings demonstrating that the PDGF-B-chain was associated with endothelium at the luminal surface of the plaque and smooth muscle-like cells within the plaque (25). Ross and coworkers used a double immunostaining technique with carotid endarterectomy specimens to detect PDGF-B protein in macrophages (26).

A number of important considerations were undertaken in the design of hybridization-specific antisense oligonucleotides to Egr-1. First, each oligonucleotide was synthesized with a phosphorothioate backbone for increased stability and potency. Second, oligonucleotides were size-matched to 15 bases; longer sequences were avoided to reduce the possibility of non-specific effects seen with longer oligonucleotides (Stein, C. A. (1996) Trends in Biotechnology 14:147–149). Third, a sequence of four consecutive guanosines was avoided in light of recent reports indicating that oligonucleotides bearing this sequence, such as those that have targeted c-myb and c-myc, inhibit proliferation by a nonantisense mechanism (27,28). Fourth, the efficacy of multiple oligonucleotides directed toward various regions of Egr-1 mRNA was assessed. Finally, a size-matched, fully phosphorothioated oligonucleotide with no sequence complementarity to any portion of Egr-1 mRNA was used as a negative control.

Design of Egr-1 antisense oligonucleotides

A panel of antisense oligonucleotides complementary to rat Egr-1 mRNA were designed to identify regions within the mRNA that were suitable target sites. Putative target sites were chosen on the basis of being encoded within regions of the mRNA that had low secondary structure and theoretically had a greater potential for inter molecular hybridisation. Such single stranded regions were identified firstly by using the Zuker algorithm for determination of free energy of RNA molecules (Zuker, M (1989) Science 244:48–52). Once a low energy secondary structure was determined, regions of low frequency intramolecular base-pairing were identified by visual examination. The oligo nucleotides used are set out in Table 1

TABLE 1

| Nucleotide Sequence of Oligonucleotides (5'->3') | | | | | | |
|---|---|---|---|---|---|---|
| E1 | CGC | CAT | TAC | CTA | GTG | (SEQ ID NO:3) |
| A/S2 | CTT | GGC | CGC | TGC | CAT | (SEQ ID NO:4) |
| E6 | CCA | GGC | TGG | CGG | TAG | (SEQ ID NO:5) |
| E7 | GAG | AAC | TGA | TGT | TGG | (SEQ ID NO:6) |
| E9 | TGT | GGT | CAG | GTG | CTC | (SEQ ID NO:7) |
| E11 | ACA | CTT | TTG | TCT | GCT | (SEQ ID NO:1) |

Uptake and stability of an Egr-1 antisense oligonucleotide by smooth muscle cells One of these oligonucleotides, E11, was radiolabeled with $^{32}P$, and assessed for its ability to associate with cultured vascular smooth muscle cells. After various times, the cultures were washed with phosphate-buffered saline and removed from the vessel by scraping. After centrifugation, the cells were transferred to Eppendorf tubes, solubilized and either counted in a scintillation counter or electrophoresed on a denaturing polyacrylamide gel.

Radiolabeled E11 associated with the cells in a time-dependent manner; maximal uptake was observed after 6 h (FIG. 1, passive). The oligonucleotide was still associated with the cells after 9 h and 24 h (FIG. 1, passive). Electrophoretic analysis indicated that the oligonucleotide did not undergo significant degradation during the course of experiment.

Egr-1 antisense oligonucleotides inhibit smooth muscle proliferation

The panel of oligonucleotides were assessed for their ability to inhibit smooth muscle cell proliferation in an assay of $^3$H-thymidine incorporation into DNA. Oligonucleotides were added to the culture supernate 6 h after the medium was changed to serum-free at a final concentration of 1 μM and incubated for a further 18 h. The cells were washed and exposed again to 1 μM oligonucleotide in medium containing a concentration of serum that would stimulate $^3$H-thymidine incorporation into DNA submaximally. After a further 24 h incubation, the cells were pulsed for 6 h with $^3$H-thymidine prior to the determination of TCA-precipitable $^3$H-thymidine incorporation into DNA.

Figure 2:
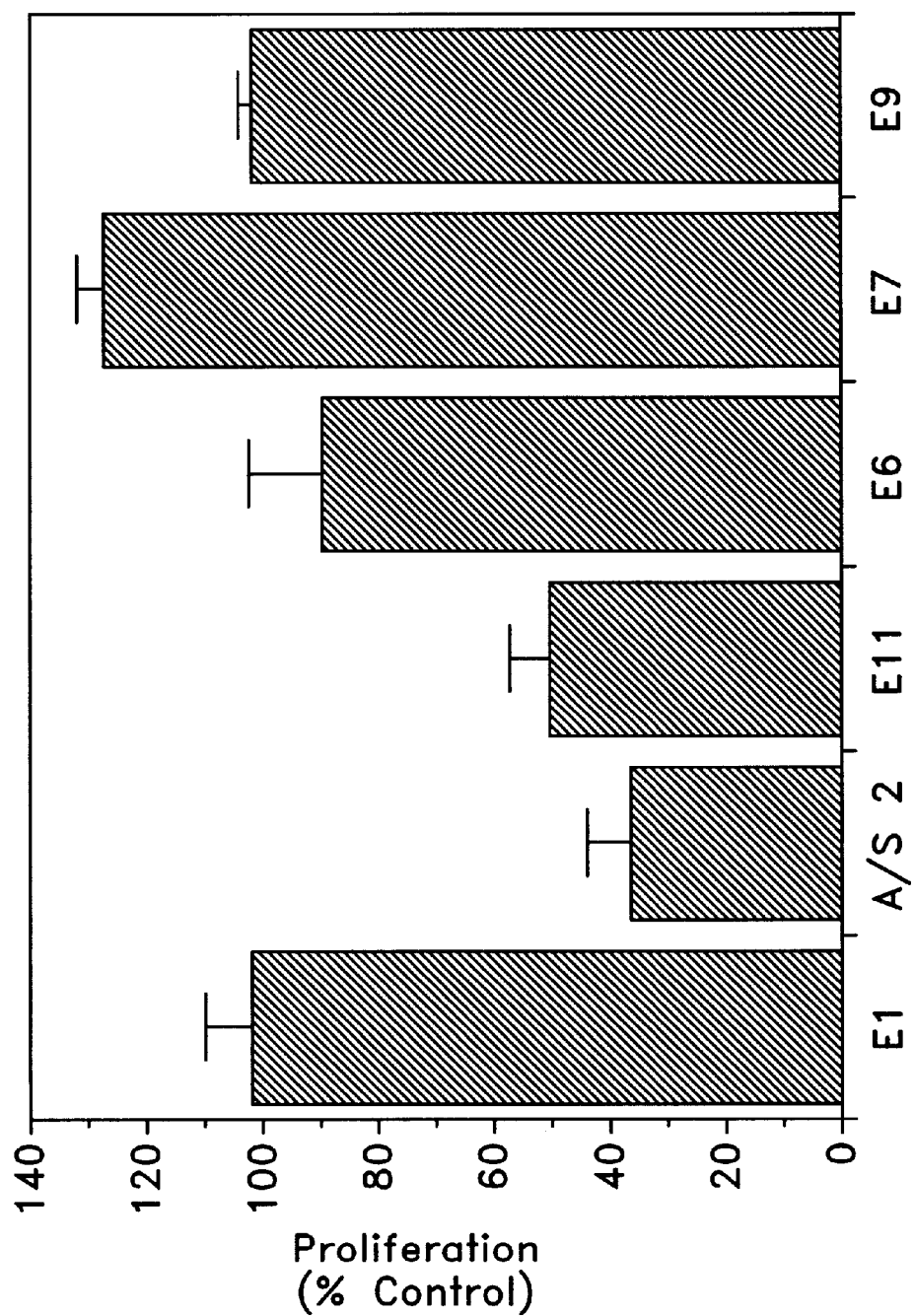
FIG. 2 shows effect of oligonucleotides (1 μM) on smooth muscle cell proliferation.

The control oligonucleotide E1, an oligonucleotide of random sequence bearing no complementarity to Egr-1 mRNA, did not alter the rate of serum-inducible $^3$H-thymidine incorporation into DNA in smooth muscle cells (n=10) (FIG. 2). In contrast, two Egr-1 antisense oligonucleotides were able to inhibit DNA synthesis. A/S2 and E11, directed against different portions of Egr-1 mRNA, inhibited by 63% (n=10), and 50% (n=12), respectively (FIG. 2). Trypan blue exclusion studies and morphologic observations revealed that inhibition was unlikely to be due to non-specific cytotoxic mechanisms. In contrast, Egr-1 antisense oligonucleotides E6, E7 or E9 failed to inhibit smooth muscle cell proliferation (FIG. 2). That not every Egr-1 antisense oligonucleotide could inhibit is consistent with the notion that naturally occurring mRNA has higher order structure and certain sequences may not be as accessible to certain oligonucleotides as others.

Egr-1 antisense oligonucleotides inhibit Egr-1 protein synthesis, but not Sp1

Western blot analysis was used to assess the effect of Egr-1 antisense oligonucleotides on levels of serum-inducible Egr-1. Oligonucleotides at a final concentration of 1 μM, were added to the culture supernates 6 h after changing the medium to serum-free to render the cells quiescent. After 16 h, the cells were washed with phosphate-buffered saline and incubated with 1 μM oligonucleotide for a further 2 h. The cells were then exposed to a concentration of serum able to stimulate $^3$H-thymidine incorporation into DNA submaximally. After 2 h, the cell lysate was electrophoresed on denaturing polyacrylamide gels prior to transfer and then assessed for the presence of Egr-1 using specific antibodies.

Serum induced the synthesis of Egr-1 protein within 2 h. Incubation of the cells with E1 did not affect the ability of serum to induce Egr-1. In contrast, E11 and A/S2 profoundly inhibited the induction of Egr-1 protein. Cellular levels of the related zinc-finger transcription factor, Sp1, were unaffected by either E11 or A/S2 demonstrating the target specificity of these oligonucleotides.

Taken together, these findings demonstrate that antisense oligonucleotides directed to selected regions of Egr-1 mRNA reduce the accumulation of the Egr-1 protein. Inhibition of Egr-1 is not due to non-specific or cytotoxic mechanisms. Cells treated with these oligonucleotides do not undergo morphologic changes or take up Trypan blue. Moreover, whereas Egr-1 protein levels are profoundly attenuated by these oligonucleotide, levels of the related zinc-finger transcription factor, Sp1, are unaffected. These oligonucleotides can selectively inhibit smooth muscle cell proliferation.

Discussion

Since Egr-1 is an inducible transcription factor with binding sites in multiple genes (9,18), these findings strongly suggest that the antiproliferative effects of these oligonucleotides may be due to selective inhibition of the expression of Egr-1-dependent genes required for proliferation, such as PDGF (9,18), bFGF (29) or cell-cycle regulatory genes (30). Egr-1 is not basally expressed in smooth muscle cells or endothelial cells of the vessel wall, unless activated by mechanical injury (18). Therefore, Egr-1 is an appropriate target for antiproliferative therapy.

The various oligonucleotides used in these studies were delivered to the cells without a carrier. Uptake is an energy-dependent process and is maximal at 37° C. (31). Phosphorothioate oligonucleotides have been found to associate with an 80 kD protein on the cell surface, consistent with receptor-mediated endocytosis (32,33). Passive delivery, however, is largely an inefficient process (34). The biologic effects of these oligonucleotides can be augmented by methodologies which facilitate more efficient delivery into cells, such as liposomes (35). Indeed, such approaches may be useful in increasing the biological potency of E11 and A/S2. The results presented herein indicate that "Lipofectamine", for example, can increase both the rate and total uptake of radiolabeled E11 (FIG. 2) without affecting the integrity of the oligonucleotide to any significant extent. Since post-angioplasty restenosis is usually focal, local delivery of these oligonucleotides may be useful in the treatment of this disease, which in the United States occurred is approximately 30–50% of the over 300,000 procedures performed in 1991 alone (36).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. M. A. Gimbrone, Jr., *Am. J. Cardiol.* 75, 67B (1995); E. Mattsson and A. W. Clowes, *Trends Cardiovas. Med.* 5, 200 (1995); R. Ross, *Nature* 362, 801 (1993).
2. M. D. Rekhter and D. Gordon, *Circ. Res.* 75, 410 (1994); E. G. Nabel, et al., *J. Clin. Invest.* 91, 1822 (1993); A. Jawien, D. F. Bowen-Pope, V. Lindner, S. M. Schwartz, A. W. Clowes, *J. Clin. Invest.* 89, 507 (1992); G. A. A. Ferns, et al., *Science* 253, 1129 (1991); M. W. Majesky, et al., *J. Cell Biol.* 11, 2149 (1990); J. N. Wilcox, K. M. Smith, L. T. Williams, S. M. Schwartz, D. Gordon, *J. Clin. Invest.* 82, 1134 (1988).
3. A. Gashler and V. P. Sukhatme, *Prog. Nucleic Acid Res. Mol. Biol.* 50, 191 (1995).

4. V. Lindner and M. A. Reidy, *Am. J. Path.* 146, 1488 (1995); M. W. Majesky, et al., *J. Cell Biol.* 11, 2149 (1990); T. B. Barrett and E. P. Benditt, *Proc. Natl. Acad. Sci. USA* 85, 2810 (1988).
5. V. Lindner and M. A. Reidy. *Am. J. Path.* 146, 1488 (1995).
6. L. Muthukrishnan, E. Warder, P. L. McNeil, *J. Cell. Physiol.* 148, 1–16 (1991).
7. L. M. Khachigian, J. W. U. Fries, M. W. Benz, D. T. Bonthron, T. Collins, *J. Biol. Chem.* 269, 22647 (1994).
8. R. P. H. Dirks, H. J. Jansen, B. van Gervan, C. Onnekink, H. P. J. Bloemers. *Nucleic Acids Res.* 23, 1119 (1995).
9. L. M. Khachigian, A. J. Williams, T. Collins, *J. Biol. Chem.* 270, 27679 (1995).
10. S. J. Ackerman, A. G. Minden, G. T. Williams, C. Bobonis, C.-Y. Yeung, *Proc. Natl. Acad. Sci. USA* 88, 7523 (1991).
11. Kozak, M. Influences of mRNA secondary structure on initiation by eukaryotic ribosomes. *Proc. Natl. Acad. Sci. USA* 1986;83:2580–2584.
12. Wagner, R., and Nishikura, K. Cell cycle expression of RNA duplex unwinding in cells. *Mol. Cell. Biol.* 1988;8:770–777.
13. Bennett, M. R., and Schwartz, S. M. Antisense therapy for angioplasty restenosis. *Circulation* 1995;92:1981–1993.
14. Marcus-Sekura, C., Woerner, A., Shinozuka, K., Zon, G., and Quinnan, G. Comparative inhibition of chloramphenicol acetyltransferase gene expression by antisense oligonucleotide analogues having alkyl triester, methyl phosphonate and phosphorothioate linkages. *Nucleic Acids Res.* 1987;15:5749–5763.
15. Cazenave, C., Stein, C., Loreau, N., Thuong, N., Neckers, L., Subasinghe, C., Helene, C., Cohen, J., and Toulme, J. Comparative inhibition of rabbit globin mRNA translation by modified antisense oligodeoxynucleotides, *Nucleic Acids Res.* 1989;17:4225–4273.
16. Sukhatme, V. P., Cao, X., Chang, L. L., Tsai-Morris, C.-H., Stamenkovich, D., Ferreira, P. C. P., Cohen, D. R., Edwards, S. A., Shows, T. B., Curran, T., Le Beau, M. M., and Adamson, E. D. A zinc-finger encoding gene corregulated with c-Fos during growth and differentiation and after depolarization. *Cell* 1988;53:37–43.
17. Tsai-Morris, C.-H., Cao, X., and Sukhatme, V. P. 5'-flanking sequence and genomic structure of Egr-1, a murine mitogen inducible zinc finger encoding gene. *Nucleic Acids Res.* 1988;16:8835–8846.
18. Khachigian, L. M., Lindner, V., Williams, A. J., and Collins, T. Egr-1-induced endothelial gene expression: a common theme in vascular injury. *Science* 1996;271:1427–1431.
19. Ferns, G. A. A., Sprugel, K. H., Seifert, R. A., Bowen-Pope, D. F., Kelly, J. D., Murray, M., Raines, E. W., and Ross, R. Relative platelet-derived growth factor receptor subunit expression determines cell migration to different dimeric forms of PDGF, *Growth Factors* 1990;3:315–324.
20. Barrett, T. B., and Benditt, E. W. Platelet-derived growth factor gene expression in human atherosclerotic plaques and normal artery wall. *Proc. Natl. Acad. Sci. USA* 1988;85:2810–2814.
21. Murry, C. E., Bartosek, T., Giachelli, C. M., Alpers, C. E., and Schwartz, S. M. Platelet-derived growth factor-A mRNA expression in fetal, normal adult, and atherosclerotic human aortas. *Circulation* 1996;93:1095–1106.
22. Rekhter, M., and Gordon, D. Does platelet-derived growth factor-A chain stimulate proliferation of arterial mesenchymal cells in human atherosclerostic plaques? *Circ. Res.* 1994;75:410–417.
23. Libby, P., Warner, S. J. C., Salomon, R. N., and Birinyi, L. K. Production of platelet-derived growth factor-like mitogen by smooth muscle cells from human atheroma. *N. Engl. J. Med.* 1988;318:1438–1438.
24. Barrett, T. B., and Benditt, E. P. Sis (platelet-derived growth factor B chain) gene transcripts are elevated in human atherosclerotic lesions compared to normal artery. *Proc. Natl. Acad. Sci. USA* 1987;84:1099–1103.
25. Wilcox, J. N., Smith, K. M., Williams, L. T., Schwartz, S. M., and Gordon, D. Platelet-derived growth factor mRNA detection in human atherosclerotic plaques by in situ hybridization. *J. Clin. Invest.* 1988;82:1134–1143.
26. Ross, R., Masuda, J., Raines, E. W., Gown, A. M., Katsuda, S., Sasahara, M., Malden, L. T., Masuko, H., and Sato, H. Localization of PDGF-B protein in macrophages in all phases of atherogenesis. *Science* 1990;248:1009–1012.
27. Burgess, T. I., Fisher, E. F., Ross, S. L., Bready, J. V., Qian, Y.-X., Bayewitch, I. A., Cohen, A. M., Herrera, C. J., Hu, S. S.-F., Framer, T. B., Lott, F. D., Martin, F. H., Pierce, G. P., Simonet, L., and Farrell, C. L. The antiproliferative activity of c-myb and c-myc antisense oligonucleotides in smooth muscle cells is caused by a nonantisense mechanism. *Proc. Nat. Acad. Sci. USA* 1995;92:4051–4055.
28. Villa, A. E., Guzman, L. A., Poptic, E. J., Labhasetwar, V., D'Souza, S., Farrell, C. L., Plow, E. F., Levy, R. J., DiCorleto, P. E., and Topol, E. J. Effects of antisense c-myb oligonucleotides on vascular smooth muscle cell proliferation and response to vessel wall injury. *Circ. Res.* 1995;76:505–513.
29. Hu, R.-M., and Levin, E. R. Astrocyte growth factor is regulated by neuropeptides through Tis 8 and basic fibroblast growth factor. *J. Clin. Invest.* 1994;93:1820–1827.
30. Hallahan, D. E., Dunphy, E., Virudachalam, S., Sukhatme, V. P., Kufe, D. W., and Weischselbaum, R. R. c-jun and Egr-1 participate in DNA synthesis and cell survival in response to ionizing radiation exposure. *J. Biol. Chem.* 1995;270:30303–30309.
31. Crooke, R. In vitro toxicology and pharmacokinetics of antisense oligonucleotides. *Anticancer Drug. Des.* 1991;6:609–646.
32. Stein, C. A., Tonkinson, J. L., Zhang, L. M. Yakubov, L., Gervasoni, J., Taub, R., and Rotenberg, S. A. Dynamics of the internalization of phosphodiester oligodeoxynucleotides in HL-60 cells. *Biochemistry* 1993;32:4855–4861.
33. Loke, S., Stein, C., Zhang, X., Mori, K., Nakanishi, M., Subashinge, C., Cohen, J., and Neckers, L. Characterization of oligonucleotide transport into living cells. *Proc. Natl. Acad. Sci. USA* 1989;86:3474–3478.
34. Spiller, D. G., and Tidd, D. M. The uptake kinetics of chimeric oligodeoxynucleotide analogues in human leukaemia MOLT-4 cells. *Anticancer Drug Des.* 1992;7:115–129.
35. Juliano, R. L., and Akhtar, S. Liposomes as a drug delivery system for antisense oligonucleotides. *Antisense Res. Dev.* 1992;2:165–176.
36. Nikod, P., and Scherrer, U. Explosive growth of coronary angioplasty: success story of a less than perfect procedure. *Circulation* 1993;87:1749–1751.

What is claimed is:

1. A method of inhibiting proliferation of cells selected from the group consisting of vascular cells, smooth muscle cells, endothelial cells and neoplasia cells, which method comprises administering locally to the cells an Egr-1 antisense oligonucleotide—in an amount sufficient to inhibit the proliferation of cells.

2. A method according to claim 1 in which the cells are smooth muscle cells.

3. A method according to claim 1 in which the oligonucleotide decreases expression of Egr-1.

4. A method according to claim 1 in which the antisense oligonucleotide is selected from the group consisting of antisense oligonucleotides having the sequence ACA CTT TTG TCT GCT (SEQ ID NO:1) and CTT GGC CGC TGC CAT SEQ ID NO:4).

5. An oligonucleotide for decreasing expression of Egr-1, the oligonucleotide consisting of the sequence ACA CTT TTG TCT GCT (SEQ ID NO:1).

6. A method of reducing the incidence of restenosis in a subject comprising administering locally to the subject an Egr-1 antisense oligonucleotide.

7. A method according to claim 6 in which the oligonucleotide decreases expression of Egr-1.

8. A method according to claim 6 in which the antisense oligonucleotide has the sequence ACA CTT TTG TCT GCT (SEQ ID NO:1) or CTT GGC CGC TGC CAT (SEQ ID NO:4).

* * * * *

SEQUENCE LISTING

<160> NUMBER OF SEQ ID NOS: 7

<210> SEQ ID NO 1
<211> LENGTH: 15
<212> TYPE: DNA
<213> ORGANISM: Artificial Sequence
<220> FEATURE:
<223> OTHER INFORMATION: Oligonucleotide

<400> SEQUENCE: 1
acacttttgt ctgct                                                    15

<210> SEQ ID NO 2
<211> LENGTH: 27
<212> TYPE: DNA
<213> ORGANISM: Artificial Sequence
<220> FEATURE:
<223> OTHER INFORMATION: Oligonucleotide

<400> SEQUENCE: 2
gctgtctcca cccacctctc gcactct                                       27

<210> SEQ ID NO 3
<211> LENGTH: 15
<212> TYPE: DNA
<213> ORGANISM: Artificial Sequence
<220> FEATURE:
<223> OTHER INFORMATION: Oligonucleotide

<400> SEQUENCE: 3
cgccattacc tagtg                                                    15

<210> SEQ ID NO 4
<211> LENGTH: 15
<212> TYPE: DNA
<213> ORGANISM: Artificial Sequence
<220> FEATURE:
<223> OTHER INFORMATION: Oligonucleotide

<400> SEQUENCE: 4
cttggccgct gccat                                                    15

<210> SEQ ID NO 5
<211> LENGTH: 15
<212> TYPE: DNA
<213> ORGANISM: Artificial Sequence
<220> FEATURE:
<223> OTHER INFORMATION: Oligonucleotide

<400> SEQUENCE: 5
ccaggctggc ggtag                                                    15

<210> SEQ ID NO 6
<211> LENGTH: 15
<212> TYPE: DNA
<213> ORGANISM: Artificial Sequence
<220> FEATURE:
<223> OTHER INFORMATION: Oligonucleotide

<400> SEQUENCE: 6
gagaactgat gttgg                                                    15

<210> SEQ ID NO 7
<211> LENGTH: 15

-continued

```
<212> TYPE: DNA
<213> ORGANISM: Artificial Sequence
<220> FEATURE:
<223> OTHER INFORMATION: Oligonucleotide

<400> SEQUENCE: 7
tgtggtcagg tgctc                                                    15
```